(12) United States Patent
Levanon et al.

(10) Patent No.: US 10,796,714 B2
(45) Date of Patent: Oct. 6, 2020

(54) METHOD AND SYSTEM FOR DIAGNOSING CORONARY ARTERY DISEASE (CAD) USING A VOICE SIGNAL

(71) Applicant: VOCALIS HEALTH LTD., Tel-Aviv (IL)

(72) Inventors: Yoram Levanon, Ramat Hasharon (IL); Yotam Luz, Moshav Talmei Yafe (IL)

(73) Assignee: VOCALIS HEALTH LTD., Tel Aviv (IL)

( * ) Notice: Subject to any disclaimer, the term of this patent is extended or adjusted under 35 U.S.C. 154(b) by 72 days.

(21) Appl. No.: 16/218,878

(22) Filed: Dec. 13, 2018

(65) Prior Publication Data

US 2019/0189146 A1 Jun. 20, 2019

Related U.S. Application Data

(60) Provisional application No. 62/598,477, filed on Dec. 14, 2017.

(51) Int. Cl.
| | | |
|---|---|---|
| *G10L 25/48* | (2013.01) | |
| *G10L 25/12* | (2013.01) | |
| *G10L 25/90* | (2013.01) | |
| *G10L 25/66* | (2013.01) | |
| *A61B 5/02* | (2006.01) | |
| *G10L 25/24* | (2013.01) | |
| *G10L 25/18* | (2013.01) | |

(52) U.S. Cl.
CPC .............. *G10L 25/48* (2013.01); *G10L 25/12* (2013.01); *G10L 25/66* (2013.01); *G10L 25/90* (2013.01); *A61B 5/02007* (2013.01); *G10L 25/18* (2013.01); *G10L 25/24* (2013.01); *G10L 2025/906* (2013.01)

(58) Field of Classification Search
CPC ..... G10L 25/48; G10L 25/00; G10L 25/0306; G10L 25/09; G10L 25/21; G10L 25/24; G10L 25/57; G10L 25/63; G10L 25/66
USPC ....... 704/246, 236, 249, 250, 255, 205, 206, 704/213, 272, 270
See application file for complete search history.

(56) References Cited

U.S. PATENT DOCUMENTS

| | | | | |
|---|---|---|---|---|
| 4,278,096 | A * | 7/1981 | Friedman | A61B 5/02 600/508 |
| 2015/0318002 | A1 * | 11/2015 | Karam | G10L 25/48 704/231 |
| 2017/0213007 | A1 * | 7/2017 | Moturu | G16H 10/60 |

OTHER PUBLICATIONS

Sachin Vernekar et al. ("A Novel Approach for Classification of Normal/Abnormal Phonocardiogram Recordings using Temporal Signal Analysis and Machine Learning", Sep. 11-14, 2016, IEEE).*

* cited by examiner

*Primary Examiner* — Qi Han
(74) *Attorney, Agent, or Firm* — The Roy Gross Law Firm, LLC; Roy Gross

(57) ABSTRACT

The present invention extends to methods, systems, for diagnosing coronary artery disease (CAD) in patients by using their voice signal comprising receiving voice signal data indicative of speech from the patient.

28 Claims, 3 Drawing Sheets

Figure 1:
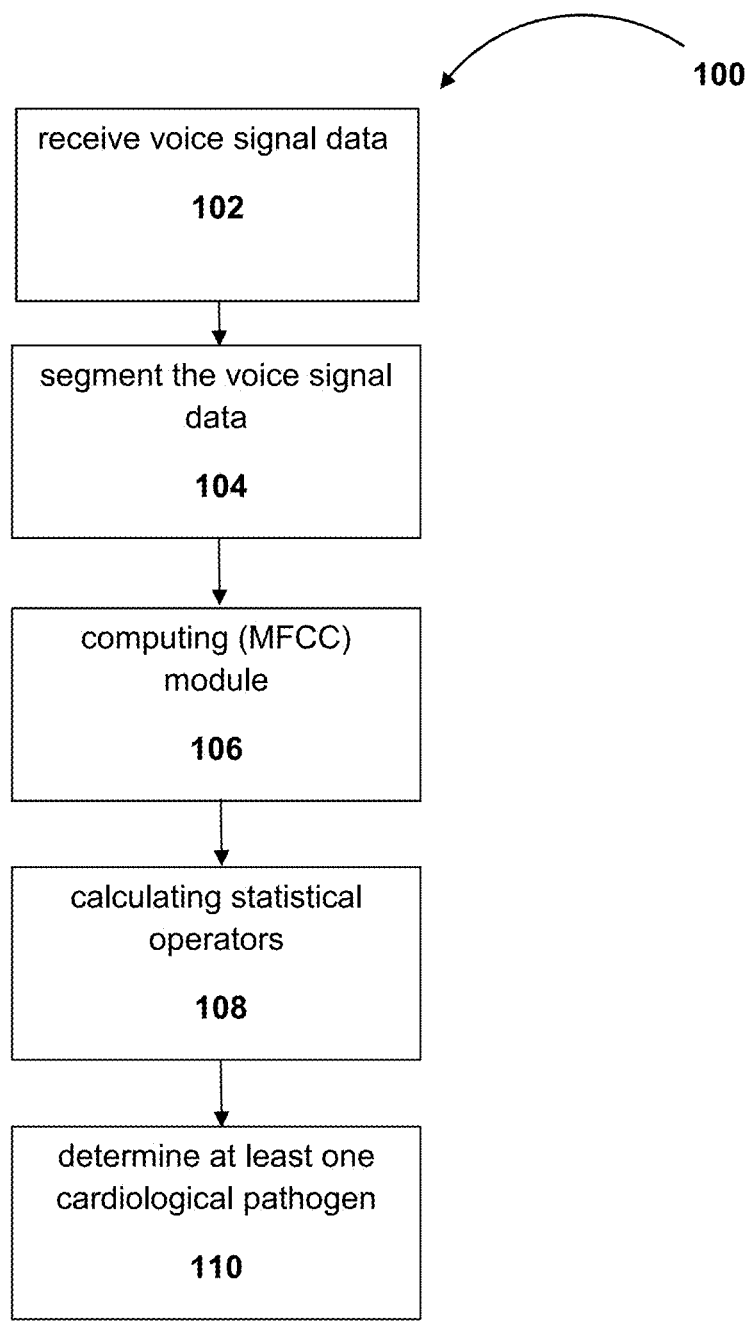

METHOD AND SYSTEM FOR DIAGNOSING CORONARY ARTERY DISEASE (CAD) USING A VOICE SIGNAL

FIELD OF THE INVENTION

The present invention generally relates to a method and system for diagnosing coronary artery disease (CAD) in patients by using their voice signal.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic, etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

Several systems and method that are deployed to diagnosing pathological phenomenon using a voice signal are known. The most commonly used feature extraction method in automatic speech recognition (ASR) is Mel-Frequency Cepstral Coefficients (MFCC) (http://recognize-speech.com/feature-extraction/mfcc). This feature extraction method was first mentioned by Bridle and Brown in 1974 and further developed by Mermelstein in 1976 and is based on experiments of the human misconception of words.

To extract a feature vector containing all information about the linguistic message, MFCC mimics some parts of the human speech production and speech perception. MFCC mimics the logarithmic perception of loudness and pitch of human auditory system and tries to eliminate speaker dependent characteristics by excluding the fundamental frequency and their harmonics. To represent the dynamic nature of speech the MFCC also includes the change of the feature vector over time as part of the feature vector. The Input for the computation of the MFFCs is a speech signal in the time domain representation with a duration in the order of 10 ms.

U.S. Pat. No. 7,398,213, Method and system for diagnosing pathological phenomenon using a voice signal, discloses a method and system for diagnosing pathological phenomenon using a voice signal. In one embodiment, the existence of at least one pathological phenomena is determined based at least in part upon a calculated average intensity function associated with speech from the patient. In another embodiment, the existence of at least one pathological phenomena is determined based at least in part upon the calculated maximum intensity function associated with speech from the patient.

For the purposes of describing and claiming the present invention, the term "crater feature" is intended to refer to a shape (on a graph of frequency vs. intensity) which manifests as a sharp drop at a first frequency continued by a relatively low level along approximately 50 Hz or more and then a relatively steep rise at a second frequency. Such crater features can be mathematically defined as points of derivatives discontinuities (a significant leap of the function derivative).

For the purposes of describing and claiming the present invention, the term "decay feature" is intended to refer to the point of highest frequency cutoff of the power spectrum density (PSD) spectrogram (with 100 frames per second).

None of the current technologies and prior art, taken alone or in combination, address nor provide a truly integrated solution in a form of diagnosing coronary artery disease (CAD) in patients by using their voice signal.

Therefore, there is a long felt and unmet need for a system and method that overcomes the problems associated with the prior art.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY OF THE INVENTION

It is thus an object of the present invention to provide a computer-implemented method for diagnosing a patient, comprising: receiving voice signal data indicative of speech from the patient; segmenting the voice signal data into frames of 32 ms with a frame shift of 10 ms; applying Mel Frequency Cepstral Coefficients (MFCC) module; computing a Cepstral representation using cosine transform; determining an existence of at least one coronary artery disease symptom associated with the patient; Mel Frequency Cepstral Coefficients (MFCC) module is applied by assigning type operator functions across the one or more of frequencies on one or more sample intensity values of the voice signal data; and an existence of at least one coronary artery disease symptom associated with the patient is determined based at least in part upon a change in intensity between at least two frequencies found in the Cepstral representation and/or calculated type operator function.

It is another object of the present invention to provide a computer-implemented system for diagnosing a patient, the system comprising: one or more processors; and a memory system communicatively coupled to the one or more processors, the memory system comprises executable instructions including: receiving voice signal data indicative of speech from the patient; segmenting the voice signal data into frames of 32 ms with a frame shift of 10 ms; applying Mel Frequency Cepstral Coefficients (MFCC) module; computing a Cepstral representation using cosine transform; determining an existence of at least one coronary artery disease symptom associated with the patient; Mel Frequency Cepstral Coefficients (MFCC) module is applied by assigning type operator functions across the one or more of frequencies on one or more sample intensity values of the voice signal data; and an existence of at least one coronary artery disease symptom associated with the patient is determined based at least in part upon a change in intensity between at least two frequencies found in the Cepstral representation and/or calculated type operator function.

The details of one or more embodiments are set forth in the accompanying drawings and the description below. Other features, objects, and advantages of the invention will be apparent from the description and drawings, and from the claims.

BRIEF DESCRIPTION OF THE PREFERRED EMBODIMENTS

Figure 2:
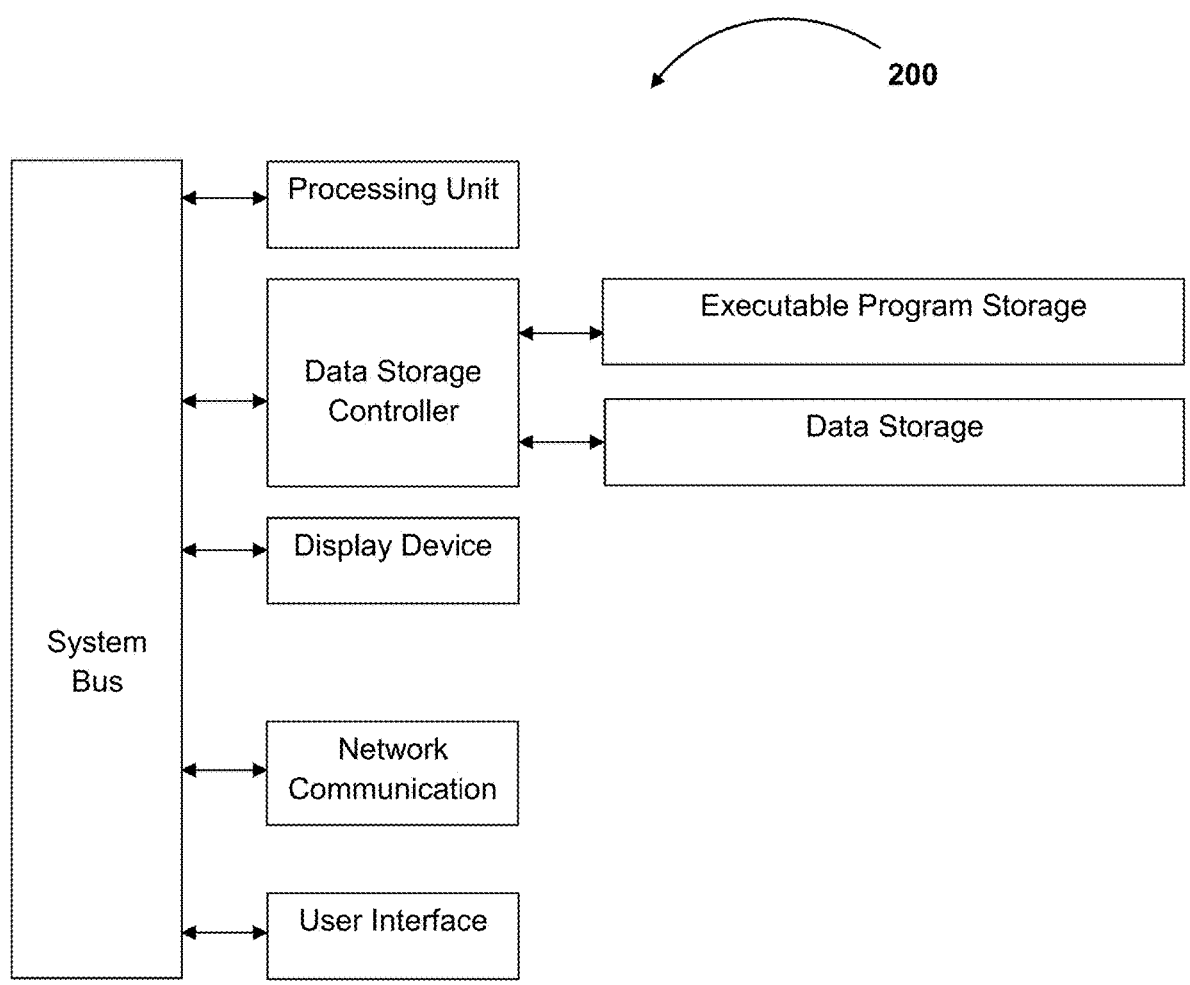
Figure 3:
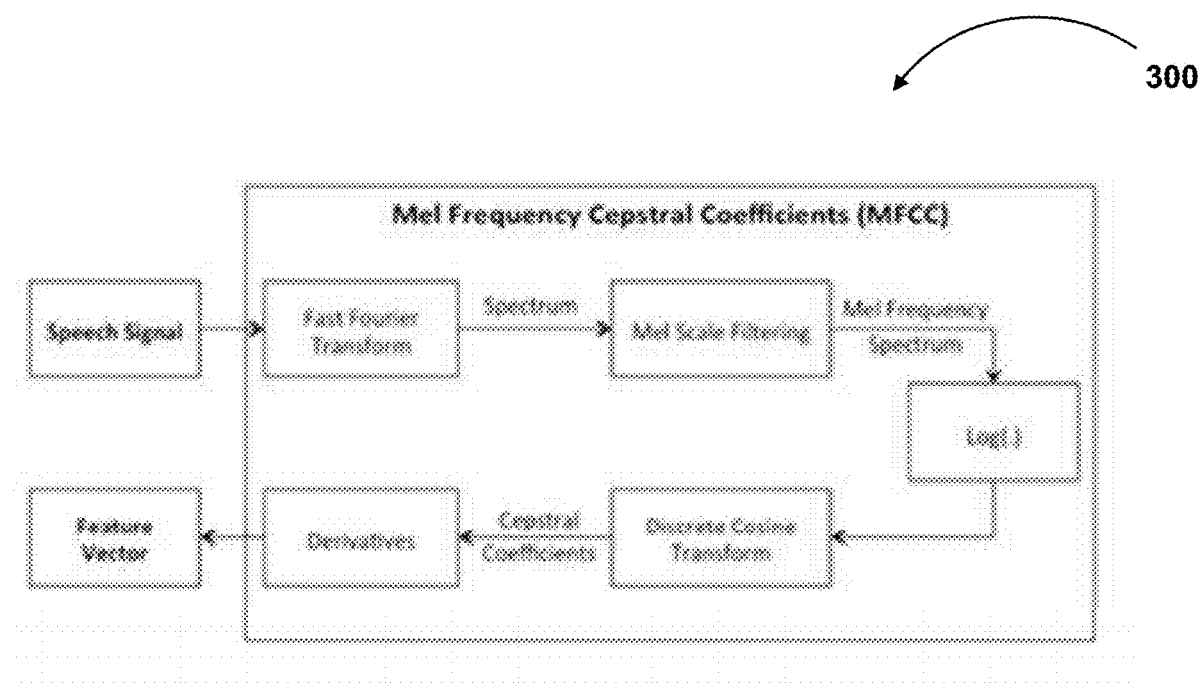

The novel features believed to be characteristics of the invention are set forth in the appended claims. The invention itself, however, as well as the preferred mode of use, further objects and advantages thereof, will best be understood by reference to the following detailed description of illustrative embodiment when read in conjunction with the accompanying drawings. In order to better understand the invention and its implementation in a practice, a plurality of embodiments will now be described, by way of non-limiting example only, with reference to the accompanying drawings, in which FIG. 1 graphically illustrates, according to another preferred embodiment of the present invention, a flow chart, according to another preferred embodiment, of the present invention method for facilitating a data processing platform;

FIG. 2 graphically illustrates, according to another preferred embodiment of the present invention, an example of computerized environment for implementing the invention; and FIG. 3 graphically illustrates, according to another preferred embodiment of the present invention, the standard implementation of computing the Mel-Frequency Cepstral Coefficients.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Unless specifically stated otherwise as apparent from the following discussions, it is appreciated that throughout the present description of embodiments, discussions utilizing terms such as "computing", "detecting," "calculating", "processing", "performing," "identifying," "determining" or the like, refer to the actions and processes of a computer system, or similar electronic computing device. The computer system or similar electronic computing device manipulates and transforms data represented as physical (electronic) quantities within the computer system's registers and memories into other data similarly represented as physical quantities within the computer system memories or registers or other such information storage, transmission, or display devices, including integrated circuits down to and including chip level firmware, assembler, and hardware based micro code.

As will be explained in further detail below, the technology described herein relates to facilitating systems and methods of speech data processing associated with cardiological pathoden including automatic analysis and representation functionality related to diagnosing coronary artery disease (CAD) in patients by using their voice signal as an input data.

While the invention is susceptible to various modifications and alternative forms, specific embodiments thereof have been shown by way of example in the drawings and the above detailed description. It should be understood, however, that it is not intended to limit the invention to the particular forms disclosed, but on the contrary, the intention is to cover all modifications, equivalents, and alternatives falling within the spirit and scope of the invention as defined by the appended claims.

A non-limiting example, the method for diagnosing a patient can be executed using a computerized process according to the example method 100 illustrated in FIG. 1. As illustrated in FIG. 1, the method 100 can first receive voice signal data 102 indicative of speech from the patient; segment the voice signal data 104 into frames of 32 ms with a frame shift of 10 ms; compute Mel Frequency Cepstral Coefficients (MFCC) module 106 to mimic the human perception of the frequency domain and/or of the power; apply various statistical feature extraction operators 108 upon the MFCC time series; determine an existence of at least one coronary artery disease symptom 110 associated with the patient. An existence of at least one coronary artery disease symptom associated with the patient is determined based at least in part upon the ratio of intensity between at least two frequency bands found in the Cepstral representation and/or its statistical properties.

Mel Frequency Cepstral Coefficients (MFCC) module is applied by assigning type operator functions across the one or more of frequencies on one or more sample intensity values of the voice signal dats and an existence of at least one coronary artery disease symptom associated with the patient is determined based at least in part upon a change in intensity between at least two frequencies found in the Cepstral representation and/or calculated type operator function. The step of segmenting the voice signal data into frames provides a power spectrum density (PSD) spectrogram with 100 frames per second. The step of applying Mel Frequency Cepstral Coefficients (MFCC) module is achieved by applying two log scaling functions that resemble the human acoustic perception: (1) to the sound frequency and (2) to the sound pressure level using a 26-channel Mel frequency triangular filters bank. The step of applying log and/or log scaling function to mimic the human perception of the power is achieved by converting to decibels (DB). For each of the one or more of frequencies each of the respective plurality of sample intensity values is separated by a time period. The voice signal data has a finite duration and each time period separating the respective plurality of sample intensity values is essentially evenly distributed within the duration of the speech. The existence of at least one coronary artery disease symptom associated with the patient is determined based at least in part upon the type operator function including at least one decay feature. The zero-crossing type operator measure provides an indicator of an intensity of the coronary artery disease symptom. The average type operator measure provides an indicator of an intensity of the coronary artery disease symptom. The maximum type operator measure provides an indicator of an intensity of the coronary artery disease symptom. The existence of at least one coronary artery disease symptom associated with the patient is determined based at least in part upon the zero-crossing and/or average and/or maximum intensity function including at least one crater feature. At least one of a height and a width of the crater feature provides an indicator of an intensity of the coronary artery disease symptom. The existence of at least one coronary artery disease symptom associated with the patient is determined based at least in part upon the zero-crossing and/or average and/or maximum intensity function including at least one table feature. Computing MFCC is performed by computing a Cepstral representation using any degree of freedom. The Cepstral representation comprises time-series is used for statistical feature extraction. The step of segmenting the voice signal data into frames, further provides a power spectrum density (PSD) and/or its Root Mean Squaring (RMS) spectrogram with any resolution between 1 to 200 frames per second. Computing Mel Frequency Cepstral Coefficients (MFCC) from a log scaling function that resemble the human acoustic perception of sounds is achieved by using any number of Mel frequency triangular filter banks. Computing Mel Frequency Cepstral Coefficients (MFCC) from a log scaling functions that resemble the human acoustic perception of sound pressure levels is achieved by converting to decibels (DB). For each of the two or more of frequency bands the intensity ratio values is manifested at a given time period. The voice signal data has a finite duration and each time period separating the respective plurality of intensity ratio values is essentially evenly distributed within the duration of the speech. The existence of at least one coronary artery disease symptom associated with the patient is determined based at least in part upon the type of statistical operator function including at least one decay feature. The zero-crossing type operator measure provides an indicator of the severity of the coronary artery disease symptom. The averaging type operator measure provides an indicator of the severity of the coronary artery disease symptom. The maximum type operator measure provides an indicator of the severity of the coronary artery disease symptom. The existence of at least one coronary artery disease symptom associated with the patient is determined based at least in part upon the zero-crossing and/or averaging and/or maximum statistical operators including at least one crater feature. At least one of a height and a width of the crater feature provides an indicator of the severity of the coronary artery disease symptom.

The input for the computation of the MFFCs is a 25-32 ms temporal window of the speech signal in the time domain representation. Using a frame shift of 10 ms creates 100 sets per second of MFCC low level features. Each high level feature described below is an operator applied on a specific MFCC coefficient time series. Feature $A_1$ is a zero-crossing measure applied to the 1st coefficient vector after smoothing.

Feature $A_2$ is an averaging type operator applied to the same vector of Feature $A_1$. Feature B is the max value operator applied on the 6th MFCC coefficient. Both Feature $A_1$ and Feature $A_2$ are statistical operators upon the $1^{st}$ MFCC, which reflects the "balance" between low and high frequency components within each frame. It is mathematically equivalent to the original 'decay' feature analysis. Feature $A_2$ demonstrates the average 'decay' measure, and Feature $A_1$ is the fluctuation frequency of the 'decay' measure. Feature B is a statistical operator which is mathematically equivalent to the original "crater" feature. It measures a crater around 300 HZ, quantifying the width and depth of that crater.

Reference is made now to FIG. 2 which graphically illustrates, according to another preferred embodiment of the present invention, an example of computerized system for implementing the invention 200. The systems and methods described herein can be implemented in software or hardware or any combination thereof. The systems and methods described herein can be implemented using one or more computing devices which may or may not be physically or logically separate from each other. Additionally, various aspects of the methods described herein may be combined or merged into other functions.

In some embodiments, the illustrated system elements could be combined into a single hardware device or separated into multiple hardware devices. If multiple hardware devices are used, the hardware devices could be physically located proximate to or remotely from each other.

The methods can be implemented in a computer program product accessible from a computer-usable or computer-readable storage medium that provides program code for use by or in connection with a computer or any instruction execution system. A computer-usable or computer-readable storage medium can be any apparatus that can contain or store the program for use by or in connection with the computer or instruction execution system, apparatus, or device.

A data processing system suitable for storing and/or executing the corresponding program code can include at least one processor coupled directly or indirectly to computerized data storage devices such as memory elements. Input/output (I/O) devices (including but not limited to keyboards, displays, pointing devices, etc.) can be coupled to the system. Network adapters may also be coupled to the system to enable the data processing system to become coupled to other data processing systems or remote printers or storage devices through intervening private or public networks. To provide for interaction with a user, the features can be implemented on a computer with a display device, such as an LCD (liquid crystal display), touch-screen; or touch-pad, virtual display, or another type of monitor for displaying information to the user, and a keyboard and an input device, such as a mouse or trackball by which the user can provide input to the computer.

A computer program can be a set of instructions that can be used, directly or indirectly, in a computer. The systems and methods described herein can be implemented using programming languages such as C, C++, Assembly, C#™, JAVA™, Flash™ ActionScript, Visual Basic™, JavaScript™, PHP, Python, XML, HTML, etc. or a combination of programming languages, including compiled or interpreted languages, and can be deployed in any form, including as a stand-alone program or as a module, component, subroutine, or other unit suitable for use in a computing environment. The software can include, but is not limited to, firmware, resident software, microcode, etc. Protocols such as TCP/UDP/ICMP/HTTP/DNS/SOAP may be used in implementing interfaces between programming modules. The components and functionality described herein may be implemented on any desktop operating system executing in a virtualized or non-virtualized environment, using any programming language suitable for software development, including, but not limited to, different versions of Microsoft Windows™, Apple™ Mac™, iOS™, Google™ Android™, Unix™/X-Windows™, Windows Mobile™, Windows Phone™, Linux™, etc.

The processing system can be in communication with a computerized data storage system. The data storage system can include a non-relational or relational data store, such as a MySQL™ or other relational database. Other physical and logical database types could be used. The data store may be a database server, such as Microsoft SQL Server™, Oracle™, IBM DB2™, SQLITE™, or any other database software, relational or otherwise. The data store may store the information identifying syntactical tags and any information required to operate on syntactical tags. In some embodiments, the processing system may use object-oriented programming and may store data in objects. In these embodiments, the processing system may use an object-relational mapper (ORM) to store the data objects in a relational database. The systems and methods described herein can be implemented using any number of physical data models. In one example embodiment, an RDBMS can be used. In those embodiments, tables in the RDBMS can include columns that represent coordinates. In the case of environment tracking systems, data representing user events, virtual elements, etc. can be stored in tables in the RDBMS. The tables can have pre-defined relationships between them. The tables can also have adjuncts associated with the coordinates.

Suitable processors for the execution of a program of instructions include, but are not limited to, general and special purpose microprocessors, and the sole processor or one of multiple processors or cores, of any kind of computer. A processor may receive and store instructions and data from a computerized data storage device such as a read-only memory, a random access memory, both, or any combination of the data storage devices described herein. A processor may include any processing circuitry or control circuitry operative to control the operations and performance of an electronic device.

The processor may also include, or be operatively coupled to communicate with, one or more data storage devices for storing data. Such data storage devices can include, as non-limiting examples, magnetic disks (including internal hard disks and removable disks), magneto-optical disks, optical disks, read-only memory, random access memory, and/or flash storage. Storage devices suitable for tangibly embodying computer program instructions and data can also include all forms of non-volatile memory, including, for example, semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The systems, modules, and methods described herein can be implemented using any combination of software or hardware elements. The systems, modules, and methods described herein can be implemented using one or more virtual machines operating alone or in combination with each other. Any applicable virtualization solution can be used for encapsulating a physical computing machine platform into a virtual machine that is executed under the control of virtualization software running on a hardware computing platform or host. The virtual machine can have both virtual system hardware and guest operating system software.

The systems and methods described herein can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks that form the Internet.

One or more embodiments of the invention may be practiced with other computer system configurations, including hand-held devices, microprocessor systems, microprocessor-based or programmable consumer electronics, minicomputers, mainframe computers, etc. The invention may also be practiced in distributed computing environments where tasks are performed by remote processing devices that are linked through a network.

Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) could be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. In some embodiments, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, watches, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Reference is made now to FIG. 3 which graphically illustrates, according to another preferred embodiment of the present invention, standard implementation of computing the Mel-Frequency Cepstral Coefficients 300. Mel Frequency Cepstral Coefficients (MFCCs) are a feature widely used in automatic speech and speaker recognition. Prior to the introduction of MFCCs, Linear Prediction Coefficients (LPCs) and Linear Prediction Cepstral Coefficients (LPCCs) were the main feature type for automatic speech recognition (ASR). Mel-frequency cepstral coefficients (MFCCs) are coefficients that collectively make up an MFC. They are derived from a type of cepstral representation of the audio clip (a nonlinear "spectrum-of-a-spectrum"). The difference between the cepstrum and the mel-frequency cepstrum is that in the MFC, the frequency bands are equally spaced on the mel scale, which approximates the human auditory system's response more closely than the linearly-spaced frequency bands used in the normal cepstrum. This frequency warping can allow for better representation of sound, for example, in audio compression. On a high level MFCCs are commonly derived by framing the signal into short frames; for each frame calculating the periodogram estimate of the power spectrum; applying the mel filterbank to the power spectra, summing the energy in each filter; taking the logarithm of all filterbank energies; taking the DCT of the log filterbank energies; and keeping DCT coefficients 2-13, discarding the rest.

While one or more embodiments of the invention have been described, various alterations, additions, permutations and equivalents thereof are included within the scope of the invention.

In the description of embodiments, reference is made to the accompanying drawings that form a part hereof, which show by way of illustration specific embodiments of the claimed subject matter. It is to be understood that other embodiments may be used and that changes or alterations, such as structural changes, may be made. Such embodiments, changes or alterations are not necessarily departures from the scope with respect to the intended claimed subject matter. While the steps herein may be presented in a certain order, in some cases the ordering may be changed so that certain inputs are provided at different times or in a different order without changing the function of the systems and methods described. The disclosed procedures could also be executed in different orders. Additionally, various computations that are herein need not be performed in the order disclosed, and other embodiments using alternative orderings of the computations could be readily implemented. In addition to being reordered, the computations could also be decomposed into sub-computations with the same results.

The invention claimed is:

1. A computer-implemented method for diagnosing a patient, comprising:
   a. receiving voice signal data indicative of speech from the patient;
   b. segmenting the voice signal data into frames of 32 ms with a frame shift of 10 ms;
   c. computing Mel Frequency Cepstral Coefficients (MFCC);
   d. applying various statistical feature extraction operators upon the MFCC time series and;
   e. determining an existence of at least one coronary artery disease symptom associated with the patient;
   wherein an existence of at least one coronary artery disease symptom associated with the patient is determined based at least in part upon the ratio of intensity between at least two frequency bands found in the Cepstral representation and/or its statistical properties.

2. The method of claim 1, wherein the step of computing MFCC is performed by computing a Cepstral representation using any degree of freedom.

3. The method of claim 1, wherein the Cepstral representation comprises time-series is used for statistical feature extraction.

4. The method of claim 1, wherein the step of segmenting the voice signal data into frames, further provides a power spectrum density (PSD) and/or its Root Mean Squaring (RMS) spectrogram with any resolution between 1 to 200 frames per second.

5. The method of claim 1, wherein the step of computing Mel Frequency Cepstral Coefficients (MFCC) from a log scaling function that resemble the human acoustic perception of sounds is achieved by using any number of Mel frequency triangular filter banks.

6. The method of claim 1, wherein the step of computing Mel Frequency Cepstral Coefficients (MFCC) from a log scaling functions that resemble the human acoustic perception of sound pressure levels is achieved by converting to decibels (DB).

7. The method of claim 1, wherein for each of the two or more of frequency bands the intensity ratio values is manifested at a given time period.

8. The method of claim 1, wherein the voice signal data has a finite duration and each time period separating the respective plurality of intensity ratio values is essentially evenly distributed within the duration of the speech.

9. The method of claim 1, wherein the existence of at least one coronary artery disease symptom associated with the patient is determined based at least in part upon the type of statistical operator function including at least one decay feature.

10. The method of claim 9, wherein the zero-crossing type operator measure provides an indicator of the severity of the coronary artery disease symptom.

11. The method of claim 9, wherein the averaging type operator measure provides an indicator of the severity of the coronary artery disease symptom.

12. The method of claim 9, wherein the maximum type operator measure provides an indicator of the severity of the coronary artery disease symptom.

13. The method of claim 9, wherein at least one of a height and a width of the crater feature provides an indicator of the severity of the coronary artery disease symptom.

14. The method of claim 1, wherein the existence of at least one coronary artery disease symptom associated with the patient is determined based at least in part upon the zero-crossing and/or averaging and/or maximum statistical operators including at least one crater feature.

15. A computer-implemented system for diagnosing a patient, the system comprising:
   a. one or more processors; and
   b. a memory system communicatively coupled to the one or more processors, the memory system comprises executable instructions including:
      i. receiving voice signal data indicative of speech from the patient;
      ii. segmenting the voice signal data into frames of 32 ms with a frame shift of 10 ms;
      iii. computing Mel Frequency Cepstral Coefficients (MFCC);
      iv. applying various statistical feature extraction operators upon the MFCC time series and;
      v. determining an existence of at least one coronary artery disease symptom associated with the patient;
   wherein an existence of at least one coronary artery disease symptom associated with the patient is determined based at least in part upon the ratio of intensity between at least two frequency bands found in the Cepstral representation and/or its statistical properties.

16. The system of claim 15, wherein the step of computing MFCC is performed by computing a Cepstral representation using any degree of freedom.

17. The system of claim 15, wherein the Cepstral representation comprises time-series is used for statistical feature extraction.

18. The system of claim 15, wherein the step of segmenting the voice signal data into frames, further provides a power spectrum density (PSD) and/or its Root Mean Squaring (RMS) spectrogram with any resolution between 1 to 200 frames per second.

19. The system of claim 15, wherein the step of computing Mel Frequency Cepstral Coefficients (MFCC) from a log scaling function that resemble the human acoustic perception of sounds is achieved by using any number of Mel frequency triangular filter banks.

20. The system of claim 15, wherein the step of computing Mel Frequency Cepstral Coefficients (MFCC) from a log scaling functions that resemble the human acoustic perception of sound pressure levels is achieved by converting to decibels (DB).

21. The system of claim 15, wherein for each of the two or more of frequency bands the intensity ratio values is manifested at a given time period.

22. The system of claim 15, wherein the voice signal data has a finite duration and each time period separating the respective plurality of intensity ratio values is essentially evenly distributed within the duration of the speech.

23. The system of claim 15, wherein the existence of at least one coronary artery disease symptom associated with the patient is determined based at least in part upon the type of statistical operator function including at least one decay feature.

24. The system of claim 23, wherein the zero-crossing type operator measure provides an indicator of the severity of the coronary artery disease symptom.

25. The system of claim 23, wherein the averaging type operator measure provides an indicator of the severity of the coronary artery disease symptom.

26. The system of claim 23, wherein the maximum type operator measure provides an indicator of the severity of the coronary artery disease symptom.

27. The system of claim 23, wherein at least one of a height and a width of the crater feature provides an indicator of the severity of the coronary artery disease symptom.

28. The system of claim 15, wherein the existence of at least one coronary artery disease symptom associated with the patient is determined based at least in part upon the zero-crossing and/or averaging and/or maximum statistical operators including at least one crater feature.

* * * * *